United States Patent [19]
DuCharme

[11] 3,961,056
[45] June 1, 1976

[54] SUBSTITUTED MORPHOLINE GUANIDINES FOR THE TREATMENT OF ARRHYTHMIC CONDITIONS

[75] Inventor: Donald W. DuCharme, Cooper Township, Kalamazoo County, Mich.

[73] Assignee: The Upjohn Company, Kalamazoo, Mich.

[22] Filed: Feb. 11, 1974

[21] Appl. No.: 441,399

[52] U.S. Cl............................ 424/248; 424/244; 424/246; 424/250; 424/263; 424/274; 424/326
[51] Int. Cl.²...................................... A61K 31/535
[58] Field of Search .................................. 424/248

[56] References Cited
OTHER PUBLICATIONS

Takashi et al., Chemical Abstracts, 59:8728(b) 1963.
Neumann et al., Chemical Abstracts, 63:4207(g) 1965.
Ozawa et al., Chemical Abstracts, 69:67319(d) 1968.
Lubas et al., Chemical Abstracts, 73:2399(t) 1970.
Honjo et al., Chemical Abstracts, 74:22854(m) 1971.
Stamkevicius et al., Chemical Abstracts, 74:125630(q) 1971.

*Primary Examiner*—Norman A. Drezin
*Attorney, Agent, or Firm*—Martin B. Barancik; Roman Saliwanchik

[57] ABSTRACT

The pharmaceutical compositions and methods of using these compositions for anti-arrhythmic and diuretic uses are disclosed for the compounds below:

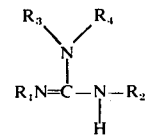

11 Claims, No Drawings

SUBSTITUTED MORPHOLINE GUANIDINES FOR THE TREATMENT OF ARRHYTHMIC CONDITIONS

BRIEF DESCRIPTION OF THE INVENTION

It has been discovered that the compounds of FIG. I are useful in the treatment of arrhythmic situations in mammals and are compounded into pharmaceutical compositions. Additionally, the compounds of this invention show diuretic activity. The compounds are formulated with pharmaceutical carriers for oral and parenteral means of administration for anti-arrhythmic and diuretic uses.

DETAILED DESCRIPTION OF THE INVENTION

In accordance with this invention, there is provided a method for treating arrhythmic situations in mammals which comprises systemically administering to said mammals a compound selected from the group consisting of

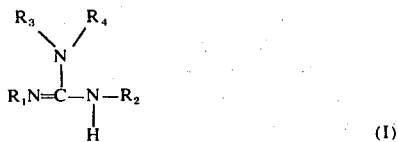

(I)

wherein $R_1$ and $R_2$ can be the same or different and are selected from the group consisting of hydrogen, alkyl of form one to eight carbon atoms, inclusive; cycloalkyl of from five to eight carbon atoms, inclusive; phenyl, phenalkyl wherein alkyl is from one to three carbon atoms, inclusive, and mono or di-substituted phenyl or phenyl moiety of the phenalkyl wherein the substituents are the same or different and are selected from the group consisting of alkyl of from one to three carbon atoms, inclusive, halogen, trifluoromethyl and alkoxy of from one to three carbon atoms, inclusive;

$R_3$ and $R_4$ are the same or different and are selected from the group consisting of hydrogen, alkyl of from one to eight carbon atoms, inclusive, cycloalkyl of from five to eight carbon atoms, inclusive, phenalkyl wherein alkyl is from one to three carbon atoms, phenyl, and mono and di-substituted phenyl or the phenyl moiety of the phenalkyl wherein the substituents are the same or different and are selected from the group consisting of alkyl of from one to three carbon atoms, alkoxy of from one to three carbon atoms, halogen and trifluoromethyl, and when $R_3$ and $R_4$ are taken together with the nitrogen atom to which they are attached form a saturated heterocyclic ring

wherein z is selected from the group consisting of methylene, NA where N is nitrogen and A is selected from the group consisting of hydrogen and alkyl of one to three carbon atoms, inclusive, oxygen, and sulfur, and when Z is methylene,

has from four to six carbon atoms and when Z is NA as previously defined, oxygen, or sulfur,

is, respectively, piperazino, N-alkylpiperazino, morpholino and thiomorpholino; and pharmaceutically acceptable acid addition salts thereof in association with a pharmaceutical carrier.

Another group of compounds, hereinafter referred to as Group A, for systemic administration comprises compounds where $R_1$ and $R_2$ are the same or different and are selected from the group consisting of alkyl of from four to seven carbon atoms, inclusive, cycloalkyl of from five to seven atoms, inclusive, phenyl, phenalkyl with alkyl of from one to three carbon atoms, inclusive, phenyl and mono-substituted phenyl and phenyl moiety of the phenalkyl wherein the substituent is selected from the group consisting of alkyl of one to three carbon atoms, inclusive, alkoxy of from one to three carbon atoms, inclusive, halogen, and trifluoromethyl;

$R_3$ and $R_4$ are the same or different and are selected from the group consisting of alkyl of from one to eight carbon atoms, inclusive, cycloalkyl of from five to seven carbon atoms, inclusive, phenyl, phenalkyl with alkyl of from one to three carbon atoms, inclusive, and mono-substituted phenyl and phenyl moiety of the phenalkyl wherein the substituent is selected from the group consisting of one to three carbon atoms, inclusive, alkoxy with one to three carbon atoms, inclusive, halogen and trifluoromethyl, and when $R_3$ and $R_4$ are taken together with the nitrogen atom to which they are attached, form a saturated heterocyclic ring,

wherein Z is selected from the group consisting of methylene, NA as defined previously, oxygen and sulfur and when Z is methylene,

has from four to six carbon atoms, and when Z is NA, oxygen, or sulfur,

is, respectively, piperazino, N-alkylpiperazino, morpholino and thiomorpholino.

A further group of compounds, hereinafter referred to as Group B, for systemic administration comprises compounds where $R_1$ and $R_2$ are the same or different and are selected from the group consisting of alkyl of from four to six carbon atoms, inclusive, cycloalkyl of five to seven carbon atoms, inclusive, phenyl, phenalkyl with alkyl of one to three carbon atoms, inclusive, mono-substituted phenyl or phenyl moiety of phenalkyl, the substituent selected from the group consisting of alkyl of one to three carbon atoms, inclusive, alkoxy of one to three carbon atoms, inclusive, halogen, and trifluoromethyl with the proviso that when $R_1$ is phenyl, phenalkyl or the mono-substituted phenyl or phenyl moiety of the phenalkyl, $R_2$ is selected from the group consisting of alkyl of four to six carbon atoms, inclusive, and cycloalkyl of five to seven carbon atoms, inclusive;

$R_3$ and $R_4$ are the same or different and are selected from the group consisting of alkyl of from four to six carbon atoms, inclusive, cycloalkyl of from five to seven carbon atoms, and $R_3$ and $R_4$ when taken together with the nitrogen atom to which they are attached, form a saturated heterocyclic ring, $$\binom{Z}{N}$$

wherein Z is selected from the group consisting of methylene, NA as previously defined, oxygen, and sulfur, and when Z is methylene, $$\binom{Z}{N}$$

is from four to six carbon atoms, and when Z is NA oxygen, or sulfur, $$\binom{Z}{N}$$

is, respectively, piperazino, N-alkylpiperazino, morpholino or thiomorpholino.

A further group of compounds, hereafter referred to as Group C, for systemic administration and composition compounding, comprise compounds where $R_1$ and $R_2$ are the same or different and are selected from the group consisting of alkyl of from four to six carbon atoms, inclusive, and cycloalkyl of from five to seven carbon atoms, inclusive;

$R_3$ and $R_4$, when taken together with the nitrogen atom to which they are attached, form a saturated heterocyclic ring, $$\binom{X}{N}$$

wherein Z is selected from the group consisting of methylene, nitrogen, oxygen and sulfur and when Z is methylene, $$\binom{Z}{N}$$

has from four to six carbon atoms, and when Z is nitrogen, oxygen, or sulfur, $$\binom{Z}{N}$$

is, respectively, piperazino, morpholino, or thiomorpholino.

All of the above groupings of compounds are preferred to be administered parenterally. Additionally, very good results are observed when Groups B and C, particularly C, are administered orally.

Preferred compounds to be used in the compositions and methods of using these compositions are N,N'-dicyclohexyl-4-morpholinecarboxamidine and hydrochloride salt, N,N'-diphenyl-4-morpholinecarboxamidine and maleate salt, N,N'-bis-(p-fluorophenyl)-4-morpholinecarboxamidine and hydrochloride salt, N,N'-bis(2,6-diethylphenyl)-4-morpholinecarboxamidine and sulfate salt, N-cyclohexyl-N'-(3,4-dichlorophenyl)-4-morpholinecarboxamidine and hydrochloride or nitrate salt.

As employed in the above disclosure and throughout the specification, the term "halogen" includes fluorine, chlorine, bromine and iodine. The term "alkyl" includes methyl, ethyl, propyl, and isomers thereof when limited to three carbon atoms. When limited to a higher number of carbon atoms, the term encompasses compounds through that number of carbon atoms and isomers thereof. "Pharmaceutically acceptable acid addition salts" include the hydrochloric, hydrobromic, hydriodic, nitric, sulfuric, phosphoric, acetic, lactic, citric, succinic, benzoic, salicylic, palmitic, oxalic, cyclohexanesulfamic and the like. "Cycloalkyl" of from five to eight carbon atoms includes cyclopentyl, cyclohexyl, cycloheptyl, and cyclooctyl.

The compounds employed in this method of treating arrhythmic conditions can be prepared by methods known in the art. For example, an appropriately substituted carbodiimide (II) is reacted under suitable conditions with an appropriately substituted amine (III) to form the guanidines (IV) included in this invention ($R_1$, $R_2$, $R_3$ and $R_4$ represent the desired groups).

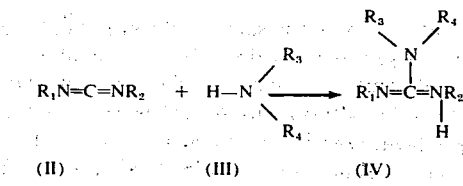

(II)　　　(III)　　　(IV)

Reaction conditions for the above reaction and other synthetic procedures for preparing guanidines and carbodiimide starting materials are well known in the art. For example, various procedures for preparing carbodiimides are outlined in F. Kurzer and K. Douraghi-Zadeh, Chem. Rev. 67, 107 (1967). Page 119 of this review article reviews some methods for adding amines to carbodiimides. When $R_1$ and $R_2$ are different, tautomers exist when the amine is added to the carbodiimide due to the mobility of the double bond. These tautomers are represented by the following equilibrium:

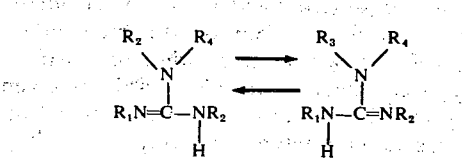

An additional reference for preparing compounds of the invention is German Pat. No. 1,192,453.

Compounds illustrative of the scope of the invention for treating arrhythmic conditions and which may be compounded into pharmaceutical compositions are below:

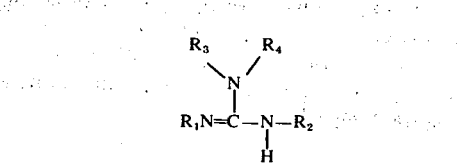

TABLE I

| $R_1$ | $R_2$ | $R_3$ | $R_4$ |
|---|---|---|---|
| $CH_3$ | $C_2H_5$ | $C_6H_5$ | $C_6H_5CH_2$ |
| $C_2H_5$ | $tC_4H_9$ | $C_6H_5C_2H_4$ | $C_6H_5O$ |
| $C_3H_7$ | $C_6H_{13}$ | 3-Cl-$C_6H_4$ | 4-($CH_3)_3C$-$C_6H_4$ |
| $iC_4H_9$ | $C_8H_{17}$ | 4-Br-3-$C_2H_5$-$C_6H_3$ | 3,5-di-$CH_3$-4-$OC_2H_5$-$C_6H_2CH_2$ |
| $CH_3$ | $C_6H_{11}$ | $C_6H_5$ | 4-$CH_3$-$C_6H_4CH_2$ |
| $iC_3H_7$ | $C_6H_5$ | $C_5H_9$ | 3,5-di-$CH_3$-$C_6H_3CH_2$ |
| $C_5H_{11}$ | $C_6H_5CH_2CH_2$ | 3,4-di-Cl-$C_6H_3$ | $C_6H_5$ |
| $C_6H_{13}$ | 3,4-di-Cl-$C_6H_3$ | | morpholino |
| $C_4H_9$ | $C_5H_9$ | | hexamethyleneimino |
| $C_6H_5$ | $C_6H_5$ | $C_6H_5$ | $C_6H_5$ |
| $C_6H_5$ | $C_6H_5$ | | morpholino |
| $C_6H_5$ | $C_6H_{11}$ | H | $C_6H_5CH_2$ |

  
 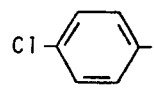 C₃H₇ CH₃
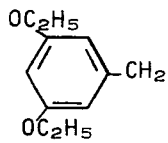 H H 
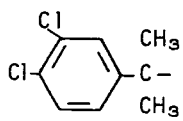 C₂H₅ C₃H₇ 
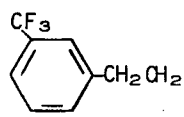   
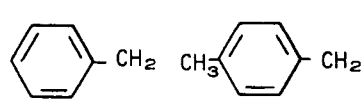 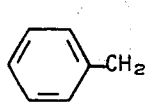 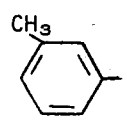
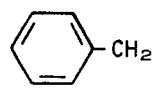 CH₃ 
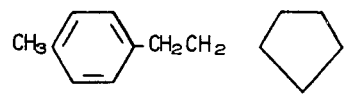 
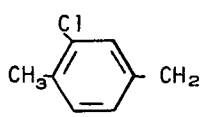  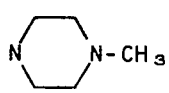
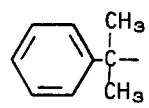 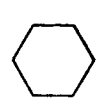 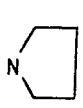
  
  CH₃ C₅H₁₁
  

Following are specific examples of compounds which can be compounded into compositions and used within the scope of this invention. These examples are not intended to be limitations upon the broad scope of the invention but merely illustrative.

Example 1

N,N'-Dicyclohexyl-4-morpholinecarboxamidine Hydrochloride

A mixture of 2.4 gm. (0.01 mole) of N,N'-dicyclohexylthiourea, 3.15 gm. (0.012 mole) of triphenylphosphine, 1.55 gm. (0.01 mole) of carbon tetrachloride, and 1.0 gm. (0.01 mole) of triethylamine in 25 ml. of methylene chloride is stirred for 2.5 hr. at 40°–45°. The reaction mixture is concentrated and the residue extracted several times with hot Skellysolve B. The combined Skellysolve B extracts are cooled to room temperature, filtered and evaporated. The crude N,N'-dicyclohexylcarbodiimide is reacted with 5 ml. of morpholine in 10 ml of tert-butyl alcohol at reflux for 16 hours. The reaction mixture is evaporated, toluene added and concentrated to remove residual morpholine. The residue is partitioned between ether and 10% hydrochloric acid. The acid layer is basified with 20% sodium hydroxide solution, nitrogen bubbled through the solution to remove ether and cooled at 5°. The product is collected, 2.07 gm. (70%), m.p. 105°–107°. The HCl salt is prepared and recrystallized from acetonitrile-ether, m.p. 226°–227°.

Anal. Calcd. for: $C_{17}H_{31}N_3O \cdot HCl$

C, 61.89; H, 9.78; N, 12.74; Cl, 10.75 Found: C, 61.91; H, 10.00; N, 12.56; Cl, 10.73

Example 2

N,N'-Diphenyl-4-morpholinecarboxamidine and Maleate Salt

Route 1 a. 2-Methyl-1,3-diphenyl-2-thiopseudourea hydriodide

A mixture of 22.8 gm. (0.1 mole) of thiocarbanilide and 17 gm. (0.12 mole) of methyl iodide in 400 ml. of ethanol is heated at reflux for 6 hours. The solvent is evaporated and residue is crystallized from ethyl acetate; 29 gm. (78%), m.p. 155°–156°.

b. Product

A mixture of 15 gm. (0.0405 mole) of 2-methyl-1,3-diphenyl-2-thiopseudourea hydriodide in 50 ml. of morpholine is heated at reflux for 16 hours. Methyl mercaptan is evolved. The reaction is concentrated in vacuo; the residue basified with 2N sodium hydroxide solution and the product extracted into ether. The dried ether layer is evaporated and the residue diluted with toluene and concentrated to remove residual morpholine. The solid is triturated with ether and the product recrystallized from acetonitrile; 6.0 g. (53%), m.p. 134°–136°.

Anal. Calcd. for: $C_{17}H_{19}N_3O$

C, 72.57; H, 6.81; N, 14.94

Found: C, 72.32; H, 6.83; N, 15.26

The maleate salt is prepared by dissolving 5.6 gm. (0.02 mole) of N,N'-diphenyl-4-morpholinecarboxamidine and 2.4 gm. (0.0207 mole) of maleic acid in methanol by warming, evaporating off the solvent and crystallizing the residue from methanol-ether; 7.7 gm. (97%), m.p. 193°–194°.

Anal. Calcd. for: $C_{17}H_{19}N_3O \cdot C_4H_4O_4$

C, 63.46; H, 5.83; N, 10.85

Found: C, 63.66; H, 5.97; N, 10.80

Route 2

A mixture of 10.6 gm. (0.05 mole) of carbanilide or 11.4 gm. (0.05 mole) of thiocarbanilide, 15.7 gm. (0.06 mole) of triphenylphosphine, 7.7 gm. (0.05 mole) of carbon tetrachloride, and 5.0 gm. (0.05 mole) of triethylamine in 25 ml. of methylene chloride is stirred for 3 hours at a water-bath temperature of 40°–45°. The reaction is concentrated and N,N'-diphenylcarbodiimide is treated with 35 ml. of morpholine in 35 ml. of dry benzene on the steam bath for 16 hours. The reaction mixture is partitioned between 350 ml. of 1N sulfuric acid and methylene chloride. Some of the sulfate crystallizes from solution and is dissolved in water. The organic layer is extracted with water. The combined aqueous acid layers are extracted with ether and basified with 20% sodium carbonate solution. Nitrogen is bubbled through the resulting suspension to remove ether. The product is collected, washed with water, dried and recrystallized from acetonitril; 10 gm. (71%), m. p. 133°–135°. This material is the same as compound obtained by Route 1, above.

Example 3

N-Cyclohexyl-N'-(3,4-dichlorophenyl)-4-morpholinecarboxamidine Hydrochloride and Nitrate Salts a. N-cyclohexyl-N'-(3,4-dichlorophenyl)thiourea A mixture of 16.2 gm. (0.1 mole) of 3,4-dichloroaniline and 14.1 gm. (0.1 mole) of cyclohexyl isothiocyanate is heated together on the steam bath for four hours. The solid is crystallized from ethanol-water; 18 gm. (59%), m.p. 159°–162°.

Anal. Calcd. for: $C_{13}H_{16}Cl_2N_2S$

C, 51.48; H, 5.32; N, 9.24

Found: C, 51.23; H, 5.06; N, 9.21 b. Product

To a solution of 5 gm. (0.05 mole) of phosgene in 100 ml. of tetrahydrofuran at 10° is added 12.1 gm. (0.04 mole) of the above thiourea in one portion. The mixture is stirred at room temperature for 16 hours. The solid which separates during the reaction period is filtered, washed with ether and dissolved in 50 ml. of chloroform. This solution is added over twenty minutes to a solution of 15 gm. (0.17 mole) of morpholine in 50 ml. of acetonitrile at 0°–10°. The reaction is stirred for 10 minutes at 0°–10°, then 2 hours at room temperature and at reflux for 2 hours. The solvent is evaporated and the residue partitioned between sodium hydroxide and ether. The ether layer is dried over potassium carbonate. After evaporating the solvent, the residue is diluted with toluene and concentrated to remove morpholine. The nitrate salt is prepared and recrystallized from acetonitrile-ether; 6.05 gm. (36%), m.p. 186°–187°.

Anal. Calcd. for: $C_{17}H_{23}Cl_2N_3O \cdot HNO_3$

C, 48.69; H, 5.77; N, 13.36; Cl, 16.91

Found: C, 48.58; H, 5.80; N, 13.82; Cl, 16.86

One gram of nitrate salt is converted to free base by dissolving in methanol-methylene chloride solution, diluting with 10% sodium carbonate solution, evaporating and partitioning of the residue between ether and water. The ether layer is dried over potassium carbonate, hydrochloride salt is prepared and recrystallized from methanolether; 0.4 gm., m.p. 189°–191°.

Anal. Calcd. for: $C_{17}H_{23}Cl_2N_3O \cdot HCl$

C, 51.98; H, 6.16; N, 10.70

Found: C, 51.81; H, 6.07; N, 10.56

Example 4

N'-(o-Chlorophenyl)-N-cyclohexyl-4-morpholine carboxamidine hydrochloride a. N-Cyclohexyl-4-morpholinecarboximidoyl chloride hydrochloride To a solution of 10 gm. (0.044 mole) of N-cyclohexylthio-4-morpholinecarboxamide in 50 ml. of dry tetrahydrofuran is added a solution of 5.2 gm. (0.052 mole) of phosgene in 50 ml. of tetrahydrofuran. The reaction is mildly exothermic, the N-cyclohexyl-4-morpholinecarboximidoyl chloride hydrochloride separating from solution within 1–2 minutes. The suspension is stirred for one hour, solid collected and washed with ether; 10.8 gm. (92%), m.p. 179°–181°.

b. Product

A solution of 10.8 gm. (0.0405 mole) of N-cyclohexyl-4-morpholinecarboximidoyl chloride hydrochloride in 50 ml. of chloroform is added at 0°–5° to a solution of 16 gm. (0.125 mole) of o-chloroaniline in 75 ml. of acetonitrile over 30 minutes. The reaction is stirred at room temperature for one hour and then heated at reflux for three hours. The mixture is concentrated; residue partitioned between ether and 10% sodium carbonate. The ether is evaporated to a mixture of o-chloroaniline and product. The mixture is transferred to a 1 kg. silica gel column, which is eluted with methylene chloride until the elution of o-chloroaniline is complete. The product is eluted from the column with 10–25% (v/v) methanol-methylene chloride. The hydrochloride salt is prepared and recrystallized from methanol-ether; 9.2 gm., m.p. 258°–259°.

Anal. Calcd. for: $C_{17}H_{24}ClN_3O \cdot HCl$
C, 56.98; H, 7.03; N, 11.73; Cl, 19.79
Found: C, 57.35; H, 7.21; H, 11.42; Cl, 19.82

Example 5

N-cycloheptyl-N'-cyclohexyl-4-morpholinecarboxamidine hydrochloride a. N-Cycloheptyl-N'-cyclohexylthiourea The thiourea is prepared by reacting 14.1 gm. (0.1 mole) of cyclohexyl isothiocyanate and 11.5 gm. (0.1 mole) of cycloheptylamine in 200 ml. of ether for 1.5 hr. at room temperature. Reaction is diluted with an equal volume of Skellysolve B to give 19.5 gm. of product, m.p. 160°–161°.

b. Product

To 5 gm. (0.05 mole) of phosgene in 110 ml. of tetrahydrofuran at 15°–25° was added 10 gm. (0.0394 mole) of N-cycloheptyl-N'-cyclohexylthiourea in one portion. The reaction is stirred for 7 hours, the solution concentrated in vacuo and residue dissolved in 35 ml. of chloroform. This solution is added to 5 gm. of sodium hydroxide in 25 ml. of water over 10 minutes at 0°–5°. The mixture is stirred for 15 minutes at 0—5°, the chloroform layer separated and combined with chloroform extracts of the cold aqueous layer. The chloroform layer is dried over potassium carbonate, evaporated and the N-cycloheptyl-N'-cyclohexylcarbodiimide distilled as a colorless oil, 6.85 gm. (78%), m.p. 134–137 (1.1 mm.).

A mixture of 6.85 gm. (0.031 mole) of N-cycloheptyl-N'-cyclohexylcarbodiimide and 7 gm. (0.08 mole) of morpholine in 10 ml. of tert.-butyl alcohol is stirred at reflux for four hours. The reaction is diluted with toluene and concentrated to remove morpholine. The residue is converted to the hydrochloride salt which is recrystallized from acetonitrile-ether, 6.1 gm., m.p. 205°–206°.

Anal. calcd. for: $C_{18}H_{33}N_3O \cdot HCl$
c, 62.86; H, 9.96; N, 12.22, Cl, 10.31
Found: C, 62.73; H, 9.89; N, 12.02, Cl, 10.32

In a manner similar to the above methods, the following compounds of this invention are prepared:

TABLE II

| $R_1$ | $R_2$ | $R_3$ | $R_4$ | Acid | M.P. |
|---|---|---|---|---|---|
| cyclohexyl | cyclohexyl | | N-(2,6-dimethylmorpholino) | ·$HNO_3$ | 237-238 |
| cyclohexyl | cyclohexyl | | piperidino | ·$HNO_3$ | 155-157 |
| cyclohexyl | cyclohexyl | | thiomorpholino | ·HCl | 255-256 |
| cyclohexyl | cyclohexyl | | pyrrolidino | ·$HNO_3$ | 141-143 |
| cyclohexyl | cyclohexyl | | piperidino | HCl | 201-202 |
| cyclohexyl | cyclohexyl | | 4-methylpiperidino | ·HCl | 169-171 |

| R₁ | R₂ | R₃ | R₄ | Acid | M.P. |
|---|---|---|---|---|---|
|  |  | | 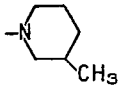 | ·(COOH)₂ | 189-191 |
|  |  | | 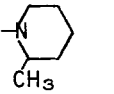 | ·HNO₃ | 159-161 |
|  |  | | 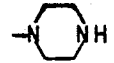 | ·2HCl | 302 |
|  |  | | 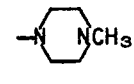 | ·2HCl | 292-293 |
|  |  | CH₃ | CH₃ | ·HCl | 232-234 |
|  |  | CH₂CH₃ | CH₂CH₃ | ·HCl | 162-164 |
|  |  | H | CH₂CH₂CH₂CH₃ | ·HNO₃ | 276-277 |
|  |  | |  | HCl | 139-140 |
|  |  | |  | HCl | 165-167 |
|  |  | |  | HCl | 170-171 |
|  |  | |  | HCl | 156-158 |
|  |  | |  | | 78-79 |

| R₁ | R₂ | R₃ | R₄ | Acid | M.P. |
|---|---|---|---|---|---|
| cyclohexyl | 2,3-dimethylphenyl | | morpholino | HNO₃ | 187-188 |
| cyclohexyl | 3-(trifluoromethyl)phenyl | | morpholino | HNO₃ | 147-148 |
| cyclohexyl | 4-chlorobenzyl | | morpholino | | 83-84 |
| cyclohexyl | 3,4-dichlorobenzyl | | morpholino | (COOH)₂ | 211-212 |
| cyclohexyl | 4-methoxyphenyl | | morpholino | | 98-99.5 |
| cyclohexyl | (CH₃)₂CHCH₂CH₂ | | morpholino | (COOH)₂ | 121-123 |
| cyclohexyl | (CH₃)₃C— | | morpholino | (COOH)₂ | 147-148 |
| phenyl | phenyl | | piperidino | HCl | 289-291 |
| benzyl | benzyl | | piperidino | | 90-92 |
| 4-chlorobenzyl | 4-chlorobenzyl | | piperidino | | 72-74 |
| 3,4-dichlorobenzyl | 3,4-dichlorobenzyl | | piperidino | (COOH)₂ | 162-164 |
| 3-methoxy-4-chlorobenzyl | 3-methoxy-4-chlorobenzyl | | piperidino | HCl | 270-272 |
| 3,4-dimethoxyphenethyl | 3,4-dimethoxyphenethyl | | piperidino | (COOH)₂ | 114-115 |
| phenethyl | phenethyl | | piperidino | HNO₃ | 102-104 |

| R₁ | R₂ | R₃ | R₄ | Acid | M.P. |
|---|---|---|---|---|---|
| $CH_3(CH_2)_3-$ | $CH_3(CH_2)_3-$ | | morpholine (N,O) | HCl | 126-127 |
| $CH_3(CH_2)_4-$ | $CH_3(CH_2)_4-$ | | morpholine (N,O) | $(COOH)_2$ | 95-96 |
| $(CH_3)_2CHCH_2CH_2-$ | $(CH_3)_2CHCH_2CH_2-$ | | morpholine (N,O) | $(COOH)_2$ | 134-136 |
| $CH_3(CH_2)_5-$ | $CH_3(CH_2)_5-$ | | morpholine (N,O) | $(COOH)_2$ | 116-118 |
| $CH_3-CH_2CH(CH_3)-CH_2-$ | $CH_3-CH_2CH(CH_3)-CH_2-$ | | morpholine (N,O) | $(COOH)_2$ | 92-93 |
| 2-methylphenyl | 2-methylphenyl | | morpholine (N,O) | ·HCl | 278-279 |
| 3-methylphenyl | 3-methylphenyl | | morpholine (N,O) | ·HCl | 253-254 |
| 4-methylphenyl | 4-methylphenyl | | morpholine (N,O) | ·HCl | 323-325 |
| 2-chlorophenyl | 2-chlorophenyl | | morpholine (N,O) | HCl | 298-299 |
| 4-chlorophenyl | 4-chlorophenyl | | morpholine (N,O) | HCl | >300° |
| 3-chlorophenyl | 3-chlorophenyl | | morpholine (N,O) | | 118-120 |
| 4-fluorophenyl | 4-fluorophenyl | | morpholine (N,O) | HCl | 303-304 |
| 3-bromophenyl | 3-bromophenyl | | morpholine (N,O) | HCl | 252-254 |
| 2,3-dichlorophenyl | 2,3-dichlorophenyl | | morpholine (N,O) | | 85-87 |
| 2,6-dimethylphenyl | 2,6-dimethylphenyl | | morpholine (N,O) | | 185-188 |

| R₁ | R₂ | R₃ | R₄ | Acid | M.P. |
|---|---|---|---|---|---|
| 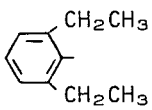 | 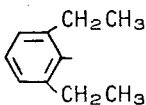 | 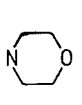 | | H₂SO₄<br>HCl | 157-159<br>208-209<br>237-240 |
| 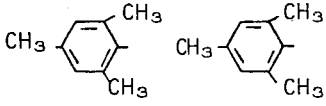 | 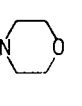 | 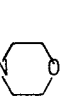 | | HCl | 288-290 |
| 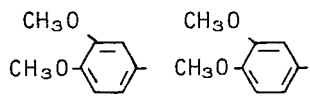 | 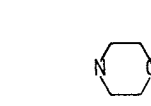 | 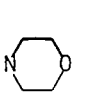 | | | 157-158.5 |
| 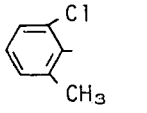 | 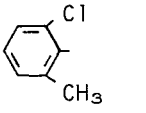 | 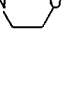 | | HCl | 304-306 |
|  | 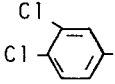 | 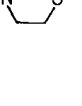 | | HCl | 264-266 |
|  | 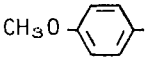 |  | | | 84 |
|  | 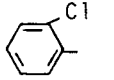 |  | | | 81-83 |

The compounds are presented for administration to humans and animals in unit dosage forms of pharmaceutical compositions such as tablets, capsules, pills, powders, granules, sterile parenteral solutions or suspensions; oral solutions or suspensions and oil-in-water or water-in-oil emulsions and suppositories containing suitable quantities of the compound.

For oral administration, either solid or fluid unit dosage forms can be prepared. For preparing solid compositions such as tablets, the compound of Formula 1 is mixed wth conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specification for the novel unit dosage forms of this invention are dictated by and directly dependent on (a) the unique characteristics of the active material and the particular effect to be achieved and (b) the limitations inherent in the art of compounding such as an active material for use in humans and animals, as disclosed in detail in this specification, these being features of the present invention. Examples of suitable unit dosage forms in accordance with this invention are tablets, capsules, pills, powder packets, wafers, granules, cachets, teaspoonfuls, tablespoonfuls, dropperfuls, ampuls, vials suppositories, segregated multiples of any of the foregoing, and other forms as herein described.

The administration of the compositions to humans and animals bring about cardioregulatory action. Arrhythmias such as auricular fibrillation, ventricular fibrillation, paroxysmal atrial or ventricular tachycardia and the like can be treated through this invention. Additionally, the compounds within this application are useful as diuretis. As such they have the property of augmenting both urine volume and sodium excretion. This effect is of particular significance where the mammal suffering cardiac abnormalities for example, arrhythmia, also has a buildup of bodily fluids.

For treating cardioregulatory problems such as arrhythmia, an effective dosage of the particular compound is employed. The particular dosage of the selected compound for treatment depends on the route of administration, the potency of the compound, as well as the size, weight, and sex of the particular mammal. For orally treating arrhythmia in mammals, the dosage is from about 10 to about 1000 mg. per day in one to four equally divided doses. A preferred dosage range is from about 40 to about 400 mg. per day. Diuresis can be observed in the range of from about 1 to about 1000 mg. per day, preferably about 10 to about 500 mg. per day. For treating arrhythmia in mammals parenterally, the dosage is from about 1 to about 500 mg. per day in one to four equally divided doses. A preferred dosage range is from about 10 to about 200 mg. per day. Diuresis can be observed in the range of from about 1 to about 500 mg. per day, preferably from about 10 to about 200 mg. parenterally.

EXAMPLE 6

A lot of 10,000 tablets, each containing 100 mg. of N,N'-dicyclohexyl-4-morpholinecarboxamidine hydrochloride is prepared from the following types and amounts of ingredients:

| | |
|---|---|
| N,N'-dicyclohexyl-4-morpholine-carboxamidine hydrochloride | 1,000 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium stearate | 10 Gm. |

The compound and dicalcium phosphate are mixed well, granulated with 7.5 percent solution of metylcellulose in water, passed through a No. 8 screen and dried carefully. The dried granules are passed through a No. 12 screen, mixed thoroughly with the talc, starch and magnesium stearate, and compressed into tablets.

These tablets are useful in treating auricular fibrillation in man at a dose of one tablet four times a day.

EXAMPLE 7

One thousand two piece hard gelatin capsules, each containing 10 mg. of N,N'-diphenyl-4-morpholinecarboxamidine maleate salt are prepared from the following types and amounts of ingredients:

| | |
|---|---|
| N,N'-diphenyl-4-morpholine-carboxamidine maleate salt | 10 Gm. |
| Dicalcium phosphate | 150 Gm. |
| Talc | 15 Gm. |
| Magnesium stearate | 1 Gm. |

The ingredients are mixed well and filled into capsules of the proper size.

Capsules so prepared are useful in preventing paroxysmal tachycardia at a dose of one capsule every four hours.

EXAMPLE 8

One thousand tablets, each containing 300 mg. of N-Cyclohexyl-N'-(3,4-dichlorophenyl)-4-morpholinecarboxamidine hydrochloride salt are prepared from the following types and amounts of ingredients:

| | |
|---|---|
| N-Cyclohexyl-N'-(3,4-dichlorophenyl)-4-morpholinecarboxamidine hydrochloride salt | 300 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful in treating auricular fibrillations in man at a dose of one tablet 3 times a day.

EXAMPLE 9

One thousand tablets, each containing 125 mg. of N'-(o-Chlorophenyl)-N-cyclohexyl-4-morpholinecarboxamidine hydrochloride are prepared from the following types and amounts of ingredients:

| | |
|---|---|
| N'-(o-Chlorophenyl)-N-cyclohexyl-4-morpholinecarboxamidine hydrochloride | 125 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful in treating paroxysml tachycardia and an increased fluid retention at a dose of 4 tablets per day.

EXAMPLE 10

A sterile preparation suitable for intramuscular injection and containing 25 mg. of N-Cycloheptyl-N'-cyclohexyl-4-morpholinecarboxamidine hydrochloride in each milliliter is prepared from the following ingredients:

| | |
|---|---|
| N-Cycloheptyl-N'-cyclohexyl-4-morpholine-carboxamidine hydrochloride | 25 Gm. |
| Benzyl benzoate | 200 ml. |
| Methylparaben | 1.5 Gm. |
| Propylparaben | 0.5 Gm. |
| Cottonseed oil q.s. | 1,000 ml. |

One milliliter of this sterile preparation is injected 4 times daily for the treatment of auricular fibrillation.

EXAMPLE 11

A sterile preparation suitable for intramuscular injection and containing 25 mg. of N,N'-Dicyclohexyl-4-morpholinecarboxamidine hydrochloride in each milliliter is prepared from the following ingredients:

| | |
|---|---|
| N,N'-Dicyclohexyl-4-morpholine-carboxamidine hydrochloride | 25 Gm. |
| Benzyl benzoate | 200 ml. |
| Methylparaben | 1.5 Gm. |
| Propylparaben | 0.5 Gm. |
| Cottonseed oil q.s. | 1,000 ml. |

Two milliliters of this sterile preparation is injected four times daily for treatment of paroxysmal tachycardia.

EXAMPLE 12

A sterile preparation suitable for intramuscular injection and containing 200 mg. of N,N'-diphenyl-4-morpholinecarboxamidine maleate salt in each milliliter is prepared from the following ingredients:

| | |
|---|---|
| N,N'-Diphenyl-4-morpholine-carboxamidine maleate salt | 200 Gm. |
| Benzyl benzoate | 200 ml. |
| Methylparaben | 1.5 Gm. |
| Propylparaben | 0.5 Gm. |
| Cottonseed oil q.s. | 1,000 ml. |

One milliliter of this sterile preparation is injected 4 times daily for treatment of auricular fibrillation and retention of bodily fluids.

EXAMPLE 13

The compounds of Table I and Table II and their acid addition salts are compounded into composition and used for the purpose of Examples 6–12. Similar results are obtained.

When the term "aralkyl" is used throughout the specification and claims, it is to be understood that the aromatic is restricted to phenyl.

Rectal dosing is with the same quantity of active compound as oral dosing. A rectal suppository can be employed to deliver the active compound where the mammal cannot be treated conveniently by means of other dosage forms, such as orally, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

I claim:

1. A method for the treatment of arrhythmic conditions in mammals which comprises administering to said mammal an anti-arrhythmic effective amount of a compound of the formula

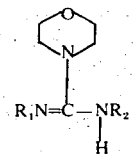

wherein $R_1$ and $R_2$ are the same or different and are selected from the group consisting of alkyl of from four to seven carbon atoms, inclusive cycloalkyl of from five to seven carbon atoms, inclusive, phenyl, phenalkyl with alkyl of from one to three carbon atoms, inclusive, and mono-substituted phenyl and phenyl moiety of the phenalkyl wherein the substituent is selected from the group consisting of alkyl of one to three carbon atoms, inclusive, alkoxy of from one to three carbon atoms, inclusive, halogen, and trifluoromethyl; and pharmaceutically acceptable acid addition salts thereof in association with a pharmaceutical carrier.

2. A method in accordance with claim 1 wherein $R_1$ and $R_2$ are the same or different and are selected from the group consisting of alkyl of from four to six carbon atoms, inclusive, cycloalkyl of five to seven carbon atoms, phenyl, phenalkyl with alkyl of one to three carbon atoms, inclusive, mono-substituted phenyl or phenyl moiety of phenalkyl, the substituent selected from the group consisting of alkyl of one to three carbon atoms, inclusive, alkoxy of one to three carbon atoms, inclusive, halogen and trifluoromethyl with the proviso that when $R_1$ is phenyl, phenalkyl or the mono-substituted phenyl or phenyl moiety of phenalkyl, $R_2$ is selected from the group consisting of alkyl of four to six carbon atoms, inclusive, and cycloaklyl of five to seven carbon atoms, inclusive.

3. A method in accordance with claim 2 wherein $R_1$ and $R_2$ are the same or different and are selected from the group consisting of alkyl of from four to six carbon atoms, inclusive, and cycloalkyl of from five to seven carbon atoms, inclusive.

4. A method in accordance with claim 1 wherein the administration is parenteral.

5. A method in accordance with claim 2 wherein the administration is parenteral.

6. A method in accordance with claim 3 wherein the administration is parenteral.

7. A method in accordance with claim 2 wherein the administration is oral.

8. A method in accordance with claim 3 wherein the administration is oral.

9. A method in accordance with claim 1 wherein the arrhythmia is tachycardia.

10. A method in accordance with claim 2 wherein the arrhythmia is tachycardia.

11. A method in accordance with claim 3 wherein the arrhythmia is tachycardia.

* * * * *